United States Patent [19]

Ruland et al.

[11] Patent Number: 4,539,160
[45] Date of Patent: Sep. 3, 1985

[54] KETENE O,O-ACETALS AND THEIR PREPARATION

[75] Inventors: Alfred Ruland, Hirschberg; Wolfgang Reuther, Heidelberg, both of Fed. Rep. of Germany

[73] Assignee: BASF Aktiengesellschaft, Fed. Rep. of Germany

[21] Appl. No.: 545,877

[22] Filed: Oct. 27, 1983

[30] Foreign Application Priority Data

Oct. 30, 1982 [DE] Fed. Rep. of Germany ....... 3240287

[51] Int. Cl.³ .................. C07C 43/313; C07D 231/12; C07D 235/04; C07D 249/08
[52] U.S. Cl. ........................... 260/465 F; 260/456 P; 548/255; 548/262; 548/333; 548/341; 548/378; 568/586; 568/592
[58] Field of Search .............. 568/592, 586; 548/255, 548/262, 378, 333, 341; 260/465 F

[56] References Cited

U.S. PATENT DOCUMENTS 4,060,623 11/1977 Meiser et al. .................. 424/269

OTHER PUBLICATIONS

Borrmann, Houben-Weyls Methoden der Organischen Chemie (Muller, Vierte Anflage, Stuttgart, 1968), pp. 362–364.

Stachel, Ber. Deut. Chem., vol. 93, pp. 1059–1063 (1960).

Primary Examiner—Alton D. Rollins
Attorney, Agent, or Firm—Keil & Weinkauf

[57] ABSTRACT

Useful novel ketene O,O-acetals of the formula I

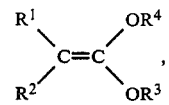

where $R^1$ is a tertiary alkyl radical of 4 to 6 carbon atoms or unsubstituted or halogen-substituted phenyl, $R^2$ is hydrogen and $R^3$ and $R^4$ independently of one another are each phenyl which is unsubstituted or substituted by halogen, alkoxy, alkyl, phenyl, phenoxy, cyano, nitro or trifluoromethyl, their preparation and their use for the preparation of ketene O,N-acetals.

3 Claims, No Drawings

KETENE O,O-ACETALS AND THEIR PREPARATION

The present invention relates to ketene O,O-acetals and a process for their preparation by eliminating water from an alpha-hydroxyacetal.

For the preparation of ketene O,O-acetals, several processes are known (D. Borrmann in Houben-Weyl-Müller, Methoden der organischen Chemie, volume 7/4, page 340 et seq., Thieme Verlag, Stuttgart 1968):

1. Elimination of hydrogen halide from an alpha-haloacetal with an alkali metal alcoholate, in particular potassium tert.-butylate. However, this process has some disadvantages. On the one hand, the process gives only ketene O,O-acetals which are unsubstituted or monosubstituted by chlorine, bromine or phenyl, low to average yields being obtained; for example, the yield of isopropyl ketene diethyl acetal is as low as 22%. On the other hand, the alcohol components are virtually exclusively simple aliphatic alcohols, such as methanol and ethanol. Furthermore, the alpha-haloacetals required for the synthesis of more highly substituted ketene O,O-acetals having phenols as OR components are unknown to date, and, because of the occurrence of various side reactions, are difficult to obtain.

2. In another conventional process, an alcohol is eliminated from an orthocarboxylic acid triester. This process too is virtually useless for the preparation of the necessary orthocarboxylates with phenols as alcohol components. This route is also unsuitable for the controlled preparation of mixed ketene O,O-acetals. The same restrictions also apply to the synthesis of ketene O,O-acetals by elimination of an alkyl hypobromide from an alpha-bromocarboxylic acid triester.

3. Conversions of 1,1-dihaloethylenes to ketene O,O-acetals are also known. However, they can be carried out successfully only in the case of beta-activated ethylenes or in the special case of 1,1-dichloroethylene, by reaction with a beta- or gamma-alkoxy alcoholate or a dialkylamino alcoholate.

We have found that ketene O,O-acetals of the formula I

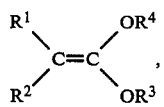

where $R^1$ is a tertiary alkyl radical of 4 to 6 carbon atoms or unsubstituted or halogen-substituted phenyl, $R^2$ is hydrogen and $R^3$ and $R^4$ independently of one another are each phenyl which is unsubstituted or substituted by halogen, alkoxy, alkyl, phenyl, phenoxy, cyano, nitro or trifluoromethyl, are very useful compounds for the preparation of the conventional (German Laid-Open Application DOS 3,100,261) ketene O,N-acetals of the formula IV

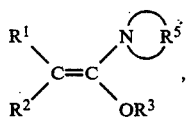

where $R^1$, $R^2$ and $R^3$ have the meanings given in claim 1 and $-NR^5$ is triazolyl, imidazolyl, benzimidazolyl or pyrazolyl. $R^1$ is, for example, tertiary butyl, $R^3$ is, for example, phenyl which is substituted by halogen (F, Cl or Br), alkoxy of 1 or 2 carbon atoms (methoxy) or alkyl of 1 to 4 carbon atoms (methyl, ethyl, propyl, i-propyl, butyl, sec.-butyl, tert.-butyl or i-butyl), polysubstitution (disubstitution or trisubstitution) by identical or different radicals being possible, eg. 4-chlorophenyl, 3,4-dichlorophenyl, 4-chloro-3-bromophenyl or 4-methyl-3-chlorophenyl, $R^4$, independently of $R^3$, has, for example, the same meanings as $R^3$, and $-NR^5$ is, for example, 1,2,4-triazol-1-yl or 1,2,3-triazol-1-yl.

The novel ketene O,O-acetals of the formula I are prepared, for example, by a method in which (a) an alpha-hydroxyacetal of the formula II

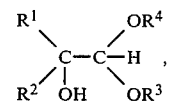

where $R^1$, $R^2$, $R^3$ and $R^4$ have the meanings stated in claim 1, is reacted with a compound

to give a compound of the formula III

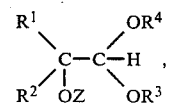

where Z is a radical $-SO_2-R$, where R is $C_1-C_4$-alkyl or $C_1-C_4$-haloalkyl, or is phenyl which is unsubstituted or monosubstituted or polysubstituted, for example by $C_1-C_4$-alkyl, (b) and the compound of the formula III is reacted with a basic compound to give the ketene O,O-acetal of the formula I as claimed in claim 1.

For example, the alpha-hydroxyacetals of the formula II are obtained by reduction of the ketones of the formula V

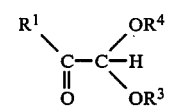

The ketones of the formula V are known, or can be prepared by a conventional process (cf. for example J. Chem. Soc. 1970, 462–464 and Liebigs Ann. Chem. 735 (1970), 145).

The reaction of a compound of the formula III with a basic compound is carried out in, for example, an aprotic dipolar solvent, such as dimethylsulfoxide, dimethylformamide or hexamethylphosphorotriamide, at from 20° to 150° C., the basic compound used being, for example, an alkali metal or alkaline earth metal hydroxide, an alkali metal or alkaline earth metal sulfide or an alkali metal, alkaline earth metal or aluminum alcoholate. The process has the great advantage that the ketones of the formula V can be readily obtained from alpha-haloketones or alpha,alpha-dihaloketones, the variety of possible OR radicals being virtually limitless. Any desired combinations can be prepared by successively introducing the $OR^3$ and $OR^4$ radicals. The reduction of the ketones of the formula V is known. The compounds of the formula III can be obtained in good or very good yields by a conventional method, for example from an alkali metal alcoholate and a sulfonyl halide.

The fact that the elimination of the —OZ group (where Z is, for example,

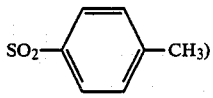

takes place smoothly, giving a virtually quantitative yield of the desired ketene O,O-acetal of the formula I, is also surprising, especially since it is known that HCl can be eliminated from an alpha-haloacetal only with difficulty and under harsh conditions.

The novel ketene O,O-acetals of the formula I are very useful for the preparation of the conventional ketene O,N-acetals of the formula II.

In this manner, it is possible to obtain the substantially pure E or Z isomers of the ketene O,N-acetals of the formula II, which can be used directly as fungicides without further purification.

EXAMPLES

Preparation of the starting compounds

A1. Tosylation of 1,1-bis-(2,4-dichlorophenoxy)-3,3-dimethylbutan-2-ol.

42.4 g (0.1 mole) of 1,1-bis-(2,4-dichlorophenoxy)-3,3-dimethylbutan-2-ol in 200 ml of absolute tetrahydrofuran were reacted with an equimolar amount of a solution of n-butyl-lithium in n-hexane at −10° C. 19.1 g (0.1 mole) of p-toluenesulfonyl chloride were then added, the mixture was allowed to thaw out at room temperature (20° C.), stirring was continued for about 1 hour, the solvent was distilled off under reduced pressure, the residue was taken up in ethyl acetate, the organic phase was washed twice with water, dried and evaporated down, and the crude product was recrystallized from cyclohexane/ethyl acetate.

Yield: 51.8 g (95% of theory)
Mp.: 87°–88° C.
$^1$H-NMR: =1.25 (s, 9H); 2.4 (s, 3H); 4.85 (d, 1H); 6.05 (d, 1H); 6.5–7.9 (m, 10H).

A2. Tosylation of 1,1-bis-(4-chlorophenoxy)-3,3-dimethylbutan-2-ol.

3 g (0.1 mole) of 80% strength sodium hydride were added to 35.6 g (0.1 mole) of 1,1-bis-4-(chlorophenoxy)-3,3-dimethylbutan-2-ol in 200 ml of absolute tetrahydrofuran, and the mixture was heated at 40° C. As soon as the evolution of gas had ceased, 19.1 g (0.1 mole) of p-toluenesulfonyl chloride were added, stirring was continued for 1 hour at room temperature, hydrolysis was effected with a little water and the mixture was then evaporated down under reduced pressure. The residue was taken up in ethyl acetate, the solution was washed twice with water, dried and evaporated down under reduced pressure, and the remaining crude product was recrystallized from ethyl acetate/cyclohexane.

Yield: 41.7 g (82% of theory)
Mp.: 97° C.
$^1$H-NMR: δ=1.25 (s, 9H); 2.3 (s, 3H); 4.8 (d, 1H); 5.8 (d, 1H); 6.5–7.9 (m, 12H).

The compounds below were prepared by the same method:

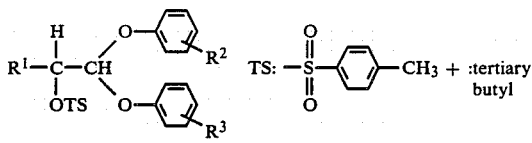

| $R^1$ | $R^2 = R^3$ | Mp. in °C. | $^1$H—NMR data (CDCl$_3$) |
|---|---|---|---|
| | 2-Cl | 79 | δ = 1.2 (s, 9H); 2.3 (s, 3H); 4.9 (d, 1H); 6.1 (d, 1H); 6.5–7.9 (m, 12H) |
| | 4-Br | 93–95 | δ = 1.2 (s, 9H); 2.3 (s, 3H); 4.8 (d, 1H); 5.8 (d, 1H); 6.5–7.9 (m, 12H) |
| | 3,5 Cl$_2$ | 124–126 | δ = 1.2 (s, 9H); 2.4 (s, 3H); 4.85 (d, 1H); 5.8 (d, 1H); 6.6–7.9 (m, 10H) |
| | 2,4,5 Cl$_3$ | 116–118 | δ = 1.2 (s, 9H); 2.35 (s, 3H); 4.85 (s, 1H); 5.95 (s, 1H); 6.8–7.9 (m, 8H) |
| ⟨⟩ | $R^2$ = 4-Cl; $R^3$ = 2-Cl | 108–110 | δ = 2.3 (s, 3H); 5.7–6 (m, 2H) 6.5–7.8 (m, 12H) |
| ⟨⟩ | $R^2$ = 2,4-Cl$_2$; $R^3$ = 4-Cl | | |

Preparation of the ketene O,O-acetals 1. 1,1-Bis-(2,4-dichlorophenoxy)-3,3-dimethylbut-1-ene 54.6 g (0.1 mole) of the tosylate of 1,1-bis-(2,4-dichlorophenoxy)-3,3-dimethylbutan-2-ol in 200 ml of dry dimethylsulfoxide were mixed with an equimolar amount of potassium tert.-butylate. The mixture was stirred for 30 minutes at room temperature, after which hydrolysis was effected with water, the mixture was extracted twice with the same volume of ethyl acetate, the extracts were dried and the solvent was distilled off under reduced pressure.

Yield: 38.57 g (95% of theory)
Bp.: 175°–176° C./0.5 mbar.
$^1$H-NMR: δ=1.2 (s, 9H); 4.85 (s, 1H); 7.73 (m, 6H).

2. 1,1-Bis-(4-chlorophenoxy)-3,3-dimethylbut-1ene 39 g (0.5 mole) of sodium sulfide were added to 47.8 g (0.1 mole) of the tosylate of 1,1-bis-(4-chlorophenoxy)-3,3-dimethylbutan-2-ol in 200 ml of dry dimethyl sulfoxide, and the mixture was stirred at 120° C. until the starting compound was no longer detectable by high-pressure liquid chromatography (HPLC). Thereafter, the mixture was cooled, water was added, the mixture was extracted twice with the same volume of ethyl acetate, the extracts were dried and the solvent was distilled off under reduced pressure.

Yield: 25.3 g (75% of theory)
$^1$H-NMR: δ=1.2 (s, 9H); 4.8 (s, 1H); 6.8–7.4 (m, 8H).

The compounds below were prepared by the same method:

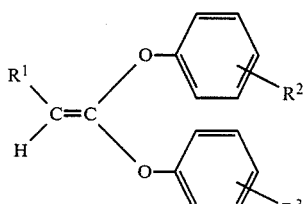

| $R^1$ | $R^2 = R^3$ | $^1$H—NMR data (CDCl$_3$) |
|---|---|---|
| + | 2-Cl | δ = 1.2 (s, 9H); 4.8 (s, 1H); 6.8–7.4 (m, 8H) |
| + | 4-Br | δ = 1.15 (s, 9H); 4.8 (s, 1H); 6.7–7.5 (m, 8H) |
| + | 3,5 Cl$_2$ | δ = 1.15 (s, 9H); 4.95 (s, 1H); 6.8–7.1 (m, 6H) |
| + | 2,4,5-Cl$_3$ | δ = 1.2 (s, 9H); 4.95 (s, 1H); 7.25–7.5 (m, 4H) |
| ⌬ | R$^2$ = 2,4-Cl$_2$; R$^3$ = 4-Cl | δ = 5.8 (s, 1H); 7.1–7.8 (m, 12H); 5.9 (s, 1H); 7.1–7.8 (m, 12H); E/Z isomer mixture |

Use of the ketene O,O-acetals of the formula I for the preparation of the ketene O,N-acetals of the formula II which are disclosed in European Patent No. 56,125.

Method

Preparation of Z-1-(1,2,4-triazol-1-yl)-1-(2,4-dichlorophenoxy)-3,3-dimethylbut-1-ene 30.4 g (0.075 mole) of 1,1-bis-(2,4-dichlorophenoxy)-3,3-dimethylbut-1-ene and 5.2 g (0.075 mole) of triazole are heated together at 180°–185° C. As soon as the reaction mixture appears homogeneous and has assumed a reddish brown coloration, the content of starting compound is determined by means of HPLC. If the desired degree of conversion has been achieved, the mixture is cooled, the product is taken up in 200 ml of a 1:1 mixture of hexane and ethyl acetate, the solution is washed 2 or 3 times with the same volume of dilute sodium hydroxide solution (5% strength) and dried with Na$_2$SO$_4$, and the solvent is distilled off under reduced pressure to give 22.2 g of ketene O,N-acetal. Isomer purity: 85% of Z-isomer, determined by means of $^1$H-NMR and HPLC.

The compounds below can be prepared in a similar manner, using the corresponding ketene O,O-acetals.

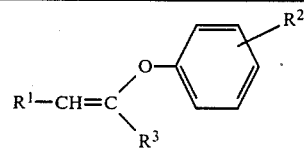

| No. | R$^1$ | R$^2$ | R$^3$ | Purity of the isomer $^1$H—NMR data (CDCl$_3$) |
|---|---|---|---|---|
| 1 | (CH$_3$)$_3$C— | 2,4-Cl$_2$ | (1,2,4-triazol-1-yl) | 85% of Z—isomer δ = 1.25 (s, 9H), 5.85 (s, 1H), 6.7–7 (m, 3H), 7.85 (s, 1H), 8.1 (s, 1H) |
| 2 | (CH$_3$)$_3$C— | 4-Cl | (1,2,4-triazol-1-yl) | 90% of Z—isomer δ = 1.25 (s, 9H), 5.9 (s, 1H), 6.8–7.4 (m, 4H), 7.95 (s, 1H), 8.2 (s, 1H) |
| 3 | (CH$_3$)$_3$C— | 2-Cl | (1,2,4-triazol-1-yl) | 90% of Z—isomer δ = 1.15 (s, 9H), 5.9 (s, 1H), 6.75–7.5 (m, 4H), 7.9 (s, 1H), 8.15 (s, 1H) |
| 4 | (CH$_3$)$_3$C— | 4-Cl | (imidazol-1-yl) | 80% of E—isomer δ = 1,25 (s, 9H), 5.25 (s, 1H), 6.7–7.7 (m, 7H) |
| 5 | (CH$_3$)$_3$C— | 2,4-Cl$_2$ | (imidazol-1-yl) | 75% of Z—isomer δ = 1.3 (s, 9H), 5.4 (s, 1H), 6.8–7.8 (m, 6H) |
| 6 | (CH$_3$)$_3$C— | 2-Cl | (imidazol-1-yl) | 80% of Z—isomer δ = 1.25 (s, 9H), 5.35 (s, 1H), 6.7–7.8 (m, 7H) |
| 7 | (CH$_3$)$_3$C— | 4-Cl | (imidazol-1-yl) | 80% of Z—isomer δ = 1.35 (s, 9H), 5.4 (s, 1H), 6.8–8.1 (m, 9H) |

We claim:

1. A ketene O,O-acetal of the formula I

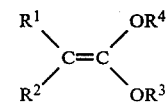

where R$^1$ is a tertiary alkyl radical of 4 to 6 carbon atoms or halogen-substituted phenyl, R$^2$ is hydrogen and R$^3$ and R$^4$ independently of one another are each phenyl which is unsubstituted or substituted by halogen, alkoxy, alkyl, phenyl, phenoxy, cyano, nitro or trifluoromethyl.

2. A ketene O,O-acetal of the formula I of claim 1, wherein R$^1$ is a tertiary alkyl radical of 4 to 6 carbon atoms.

3. A ketene O,O-acetal of the formula I of claim 1, wherein R$^1$ is tertiary butyl.

* * * * *